(12) United States Patent
Hynes et al.

(10) Patent No.: US 6,368,330 B1
(45) Date of Patent: *Apr. 9, 2002

(54) APPARATUS FOR FRAMELESS STEREOTACTIC SURGERY

(75) Inventors: Brian Hynes, Montréal; André Olivier, Cutremont, both of (CA)

(73) Assignee: Hybex Surgical Specialties Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/507,665

(22) Filed: Feb. 22, 2000

Related U.S. Application Data

(63) Continuation of application No. 09/152,243, filed on Sep. 11, 1998, now Pat. No. 6,117,143.

(51) Int. Cl.[7] .............................................. A61B 19/00
(52) U.S. Cl. ........................................ 606/130; 600/429
(58) Field of Search ..................... 606/130, 1; 600/417, 600/429, 411, 414; 604/93, 117, 174

(56) References Cited

U.S. PATENT DOCUMENTS

| | | |
|---|---|---|
| 3,357,431 A | 12/1967 | Newell |
| 4,465,069 A | 8/1984 | Barbier et al. |
| 4,805,615 A | 2/1989 | Carol |
| 4,955,891 A | 9/1990 | Carol |
| 5,443,464 A | 8/1995 | Russel et al. |
| 5,618,288 A | 4/1997 | Calvo |
| 5,649,936 A | 7/1997 | Real |
| 5,695,501 A | 12/1997 | Carol et al. |
| 5,824,007 A * | 10/1998 | Faraz et al. ................. 606/130 |
| 5,891,157 A | 4/1999 | Day et al. |
| 5,916,164 A | 6/1999 | Fitzpatrick et al. |
| 6,110,182 A * | 8/2000 | Mowlai-Ashtiani ......... 606/130 |

FOREIGN PATENT DOCUMENTS

| | | |
|---|---|---|
| EP | 0832611 A | 4/1998 |
| WO | 9740764 A | 11/1997 |

OTHER PUBLICATIONS

"A New Head Clamp for Stereotactic and Intracranial Procedures" by Andre Oliver, and Gilles Bertrand; Dept. of Neurology and Neurosurgery, Montreal Neurological Institute, McGill University, Montreal, QC, Canada 1983.

"Accessories for Neurosurgery", 1965.

"True Stereo taxis Made Easy . . . " by Mayfield/Acuss. 1997.

"Vector Vision—The power of unlimited surgical tacking" by BrainLAB. 09/1997.

"Diagnostic Operative Techniques in the Treatment of Epilepsy: Death Electrodes" by Andre Olivier. Chapter 102 from "Operative Neurological Techniques" by Schmidek, pp. 1271–1285. 1995.

* cited by examiner

Primary Examiner—Kevin Truong
(74) Attorney, Agent, or Firm—John R. S. Orange; Orange Chari

(57) ABSTRACT

This apparatus comprises a rigid half circular headclamp, three fixation pins to firmly secure the clamp to the patient's skull, a connector to firmly secure the clamp to a surgical table on which the patient rests, an articulate arm including clampable joints, secured to the headclamp in one of several possible positions and a double chuck secured to the distal end of the articulated arm. The double chuck has two ball collets arranged in side by side cavities in the chuck body, and two locking screws for each ball collet. A first locking screw releasably locks the ball collet in a selected orientation, a second separate locking screw releasably locks in an adjusted axial position an elongated instrument inserted through said collet. The first and second locking screws are actuated independently of each other. A computer guided probe and a large number of surgical instruments can be slidably inserted within the ball collets and locked in an adjusted axial position and in a selected orientation.

21 Claims, 7 Drawing Sheets

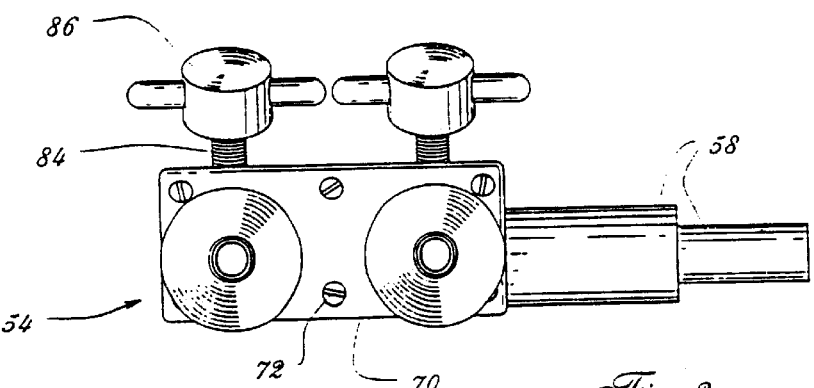
Fig. 3
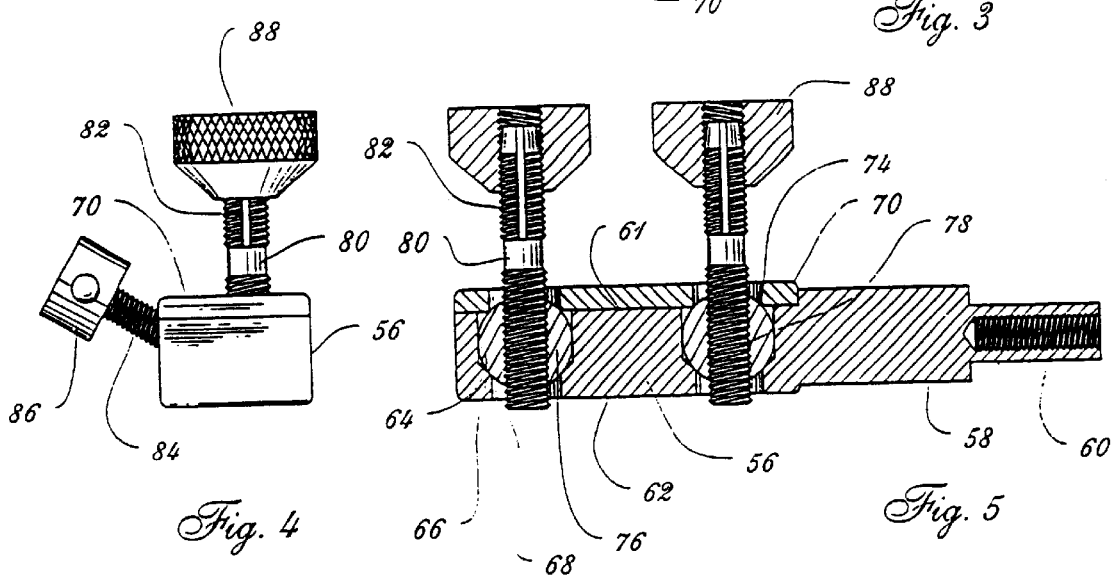
Fig. 4
Fig. 5

APPARATUS FOR FRAMELESS STEREOTACTIC SURGERY

This is a continuation of U.S. application Ser. No. 09/152,243 filed Sep. 11, 1998 now U.S. Pat. No. 6,117,143.

FIELD OF THE INVENTION

The present invention relates to an apparatus and to instruments for frameless stereotactic surgery and computer aided surgery.

BACKGROUND OF THE INVENTION

Various type of apparatuses are known for precisely positioning and for orientating a surgical instrument with relation to a patient's skull. The instrument may be inserted into the brain down to a precise location for taking a biopsy or for recording an epileptic site by an electrode of for other similar surgical procedures.

In an article published in the Journal of Applied Neuro-Physiology, Volume 46, pages 272 to 275, (1983) and entitled "A new headclamp for stereotactic and intracranial procedures", André Olivier, M.D. one of the present co-inventors and Gilles Bertrand, M.D. describe a semi-circular headclamp to be fixed to the patient'head for stereotactic and intracranial procedures. This headclamp, which is a part of the apparatus in accordance with the present invention, was then used in combination with the previously known Leksell stereotactic frame.

An advertising leaflet published in 1965 and entitled "Accessories for neurosurgery", describes a headclamp made of two pivoted parts with three spring loaded pins to engage the patient's skull and secure the headclamp in position on the skull. This headclamp, made by American Sterilizer is designed for use with three basic neuro attachments more particularly illustrated in the document.

U.S. Pat. No. 4,465,069 dated Aug. 14, 1984, entitled "Cranial insertion of surgical needle utilizing computer-assisted tomography", inventors: Jean-Yves Barbier and Christopher J. Moran describes a ring secured to the patient's head by rubber cushions and secured to the operating table by a ring mount. An instrument guide is adjustably supported by the ring.

U.S. Pat. No. 4,805,615 dated Feb. 21, 1989, entitled "Method and apparatus for performing stereotactic surgery", inventor: Mark P. Carol, describes and illustrates a positioning fixture which is designed to be secured to the patient's skull by means of self-tapping screws. The positioning fixture carries a ball collet which can be secured in any selected orientated position by a set screw. The ball collet has a through bore for slidable insertion of a surgical instrument, such as a pin.

U.S. Pat. No. 4,955,891 dated Sep. 11, 1990, entitled "Method and apparatus for performing stereotactic surgery", inventor: Mark P. Carol shows basically the same positioning device as in the previously noted U.S. Pat. No. 4,805,615.

U.S. Pat. No. 5,443,464 dated Aug. 22, 1995, entitled "External fixator apparatus", co-inventors: Thomas A. Russell and Harry E. Lee Jr., describes an apparatus for stabilizing bone fractures which includes a double chuck with ball collets and retaining nuts, to receive two retaining pins. Each ball collet has slits and both the axial position and the orientation of a pin is locked by a single retaining nut.

U.S. Pat. No. 5,618,288 dated Apr. 8, 1997, entitled "Stereotactic system for surgical procedures", inventor: Antonio M. Calvo, describes a frame which is secured to the patient's head by a plurality of fixing screws and which supports an arc-shaped member on which a slider is mounted to guide and hold a surgical instrument.

U.S. Pat. No. 5,649,936 dated Jul. 22, 1997, entitled "Stereotactic guide apparatus for use with neurosurgical headframe", inventor: Douglas D. Real, describes another type of apparatus for guiding a surgical instrument with precision within the patient's skull.

U.S. Pat. No. 5,695,501 dated Dec. 9, 1997, entitled "Apparatus for neurosurgical stereotactic procedures", co-inventors: Mark Carol, James L. Day, Erik G. Miller and Robert J. Riker, describes an apparatus for guiding a surgical instrument to a selected target within a patient's skull and along any selected path. The apparatus includes a positioning device similar to the one described in previous noted U.S. Pat. Nos. 4,805,615 and 4,955,891, and a headclamp to secure the patient's head with respect to the operating table or chair. An articulated arm is secured to the headframe and supports at its distal end a probe holder which has a ball and socket mechanism and an adjustment ball; probe holder may be maneuvered about a patient's head and selectively locked into position for path evaluation, surgical instrument guidance or attachment of the hemispheric system. However, this arrangement does not provide a positioning device which may position with great precision a surgical instrument with its tip at a desired target within the patient's brain.

OBJECTS OF THE INVENTION

The general object of the present invention is to provide a frameless stereotactic guiding system which has maximum accessibility to all the surface of the patient's skull.

Another object of the present invention is to provide a guiding apparatus of the character described which provides for skull penetration at two or more locations at the same time and with great precision, thanks to a computer assisting assembly.

Another object of the present invention is to provide an apparatus of the character described which is very easy to manipulate.

Another object of the present invention is to provide a chuck to hold a surgical instrument in a precise spatial position.

Another object of the present invention is to provide a chuck which is used as a guide for precise and safe skull penetration by a surgical instrument.

Another object of the present invention is to provide a double chuck which uses one chuck for holding a stabilizing pin while a surgical instrument is guided through the other chuck.

Another object of the present invention is to provide a chuck in which an instrument orientation is set by a first locking device and an instrument axial position is set by a second, independently actuated, locking device.

Another object of the present invention is to provide a double chuck to which a stabilizing stop pin can be secured in one chuck while guiding a drill through the other chuck.

SUMMARY OF THE INVENTION

The frameless stereotactic apparatus of the present invention comprises a rigid half circular headclamp, at least three fixation pins carried by said headclamp spaced from one another and extending inwardly thereof toward the center of the latter, said fixation pins for application to a patient's skull to secure said clamp on said skull in outwardly spaced position therefrom, a connector carried by one end of said clamp to firmly secure said clamp to a patient support surface, an articulated arm having a proximal end and a distal end, an attachment device carried by sad proximal end and securing said articulated arm to said headclamp, a double chuck device secured to the distal end of said articulated arm, said articulated arm including arm sections and clampable joints to secure said chuck in any spatial position close to said patient skull, said chuck including a body, a ball collet in said body, said ball collet capable of axially guiding an elongated surgical instrument, a first locking device to releasably lock said ball collet in a selected orientation and a second locking device to releasably lock said elongated instrument in a selected axial position, said first and second locking devices actuated independently of each other.

Preferably, said clamp has a plurality of spaced inwardly threaded through bores extending radially toward the center of said headclamp, said attachment device capable of being secured into any one of said through bores.

Preferably, said fixation pins have an externally threaded cylindrical body capable of being secured into any one of said through bores.

Preferably, said fixation pins include a spring loaded ratchet device to limit the pressure exerted by said pins on the patient's skull.

Preferably, said connector is a starburst connector.

The present invention is also directed to a stereotactic guide apparatus for use with a neurosurgical headclamp and comprising an articulated arm having a proximal and a distal end, an attachment device carried by said proximal end for securing said arm to said headclamp, a double chuck device secured to the distal end of said articulated arm, said arm including arm sections and clampable joints to secure said chuck in a predetermined spatial position close to a patient's head, said chuck including a body, a ball collet freely rotatable about its center in said body, said ball collet capable of axially guiding an elongated surgical instrument therethrough, a first locking device to releasably lock said ball collet in a selected orientation and a second locking device to releasably lock said elongated instrument in a selected axial position, said first and second locking devices actuated independently of each other.

The present invention is also directed to a double chuck for neurosurgical stereotactic procedures which comprises a body, a body extension to firmly secure said body to the distal end of an articulated arm, the body having a quadrangular cross-section with opposite base faces and two opposites side faces, a cylindrical body cavity having a first, circular, cavity opening at one of said two base faces, a cover plate removably covering the other one of said two base faces and having a second, circular, cavity opening in register with said first cavity opening, said first and second, circular, cavity openings having a smaller diameter than the diameter of said cylindrical body cavity, a ball member having a diametral through bore, located in said body cavity with a sliding fit and free to rotate about its center, a ball tightening member carried by said body, and protruding from one of said side faces to clamp said ball member in a selected oriented position of its through bore, a sleeve extending within said through bore and firmly secured to said ball member, said sleeve having an externally threaded, longitudinally slit, free end portion protruding from said body through at least one of said cavity openings and a locking nut surrounding and threaded on said free end portion and having an interfering fit with said slit free end portion to clamp in a selected longitudinal position, a surgical instrument of a cross-sectional size and shape to have a sliding fit with the inside of said sleeve, whereby the precise orientation and the longitudinal position of said instrument relative to said body can be successively and independently effected by respectively actuating said ball tightening member and said locking nut.

Preferably, there are two chucks, as above defined, disposed side by side within said body.

The present invention is also directed to a fixation pin for attaching a headclamp on a patient's skull during stereotactic surgery and comprising an externally threaded cylindrical body having a proximal end and a distal end, a pointed tip forming said proximal end, a pair of annular cooperating sets of ratchet keys coaxial with said body, one set forming said distal end of said body, the other set forming a floating annular member, a guiding rod on which said other set is axially guided and keyed, said guiding rod axially moveable, guided by and rotatably mounted within said end of said body, a cylindrical externally threaded enlargement, outwardly spaced from said floating ring and secured to said guiding rod, a compression spring surrounding said guiding rod intermediate said enlargement and said floating ring and urging the latter into engagement with said one set of ratchet teeth, an operating sleeve-like knob screwed on said enlargement, freely surrounding said sets of ratchet teeth and rotatably engaging said body and a locking screw to secure said operating knob in an axially adjusted position on said guiding rod, whereby the compression force exerted by said compression spring on said floating annular member can be adjusted.

The invention is also directed to a ruler guide for use during stereotactic procedures comprising a body having first and second parallel end faces and a through bore normal to said end faces, a tubing fixed to said body and protruding from said first end face in a first direction, said tubing coaxial with and communicating with said through bore, a graduated ruler strip secured to said body and protruding from said second end face in a second direction opposite to said first direction, said strip having an edge parallel with and close to the axis of said through bore, said ruler strip calibrated to indicate the distance from said second end face of a selected point on a surgical instrument inserted within said through bore and within said tubing.

The invention is also directed to a twisted drill for fitting the rotatable chuck of a hand held power drilling tool comprising a helically fluted cylindrical body with a rotatably chuck engaging head, said body adapted to slidably fit within a guiding sleeve, said head inwardly tapered toward said body and defining a distal free edge which is solely gripped by said rotatable chuck so that said body may become inclined relative to the rotating axis of said rotatable chuck.

Preferably, said head has a polygonal cross-section.

Preferably, a stop collar surrounds and is slidable on said body and a manually actuated releasable clamping device is carried by said collar to releasably clamp said collar in a longitudinally adjusted position on said body.

The invention is further directed to a scalp punch for use in stereotactic surgery, which comprises a cylindrical rod having a proximal end and a distal end, said proximal end defining a central recess with an annular cutting edge surrounding said recess.

BRIEF DESCRIPTION OF THE ANNEXED DRAWINGS

In the annexed drawings:

FIGS. 3, 4 and 5 are a side elevation, an end elevation and a longitudinal section, respectively, of the double chuck in accordance with the present invention;

DETAILED DESCRIPTION OF THE PREFERRED EMBODIMENT

Figure 1:
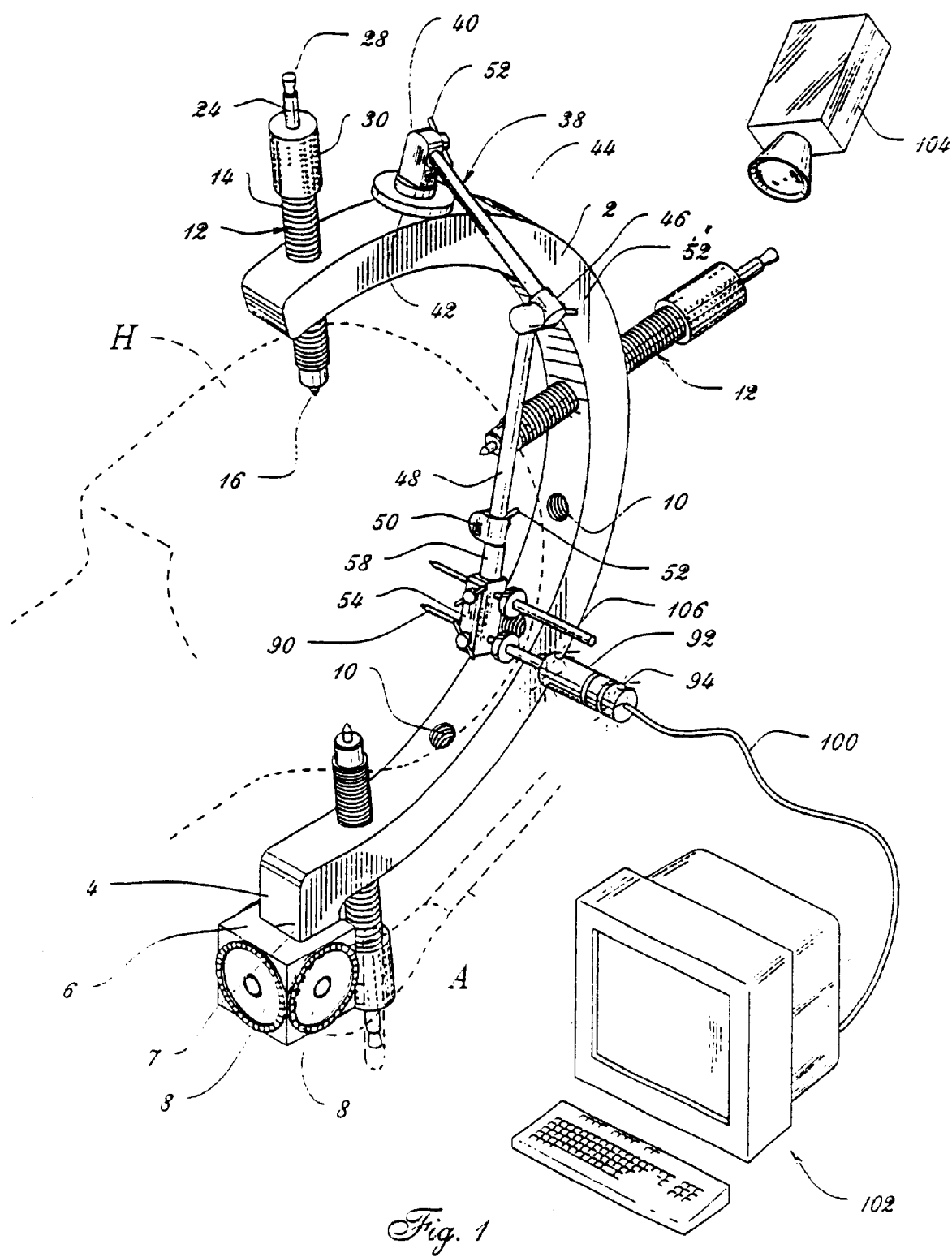
FIG. 1 is a perspective view of the apparatus of the present invention as used with a conventional computer aided guiding system.

Referring to FIG. 1, a semi-circular, rigid, headclamp 2 is designed to spacedly surround the patient's head H. Headclamp 2 has an angled end portion 4 inserted within a starburst connector 6 of known construction and formed by a square block with a notch 7 into which end portion 4 is inserted and secured. The starburst connector block includes a toothed ring 8 on each of its three faces for selective connection to an arm A fixed to a multi-movement chair or to an operating table (not shown).

Headclamp 2 has angularly spaced radial inwardly threaded through bores 10 for selectively receiving at least three fixation pins 12, which are inwardly directed from the headclamp and engage the patient's skull at right angles to one another to firmly secure the head within the headclamp 2.

Figure 6:
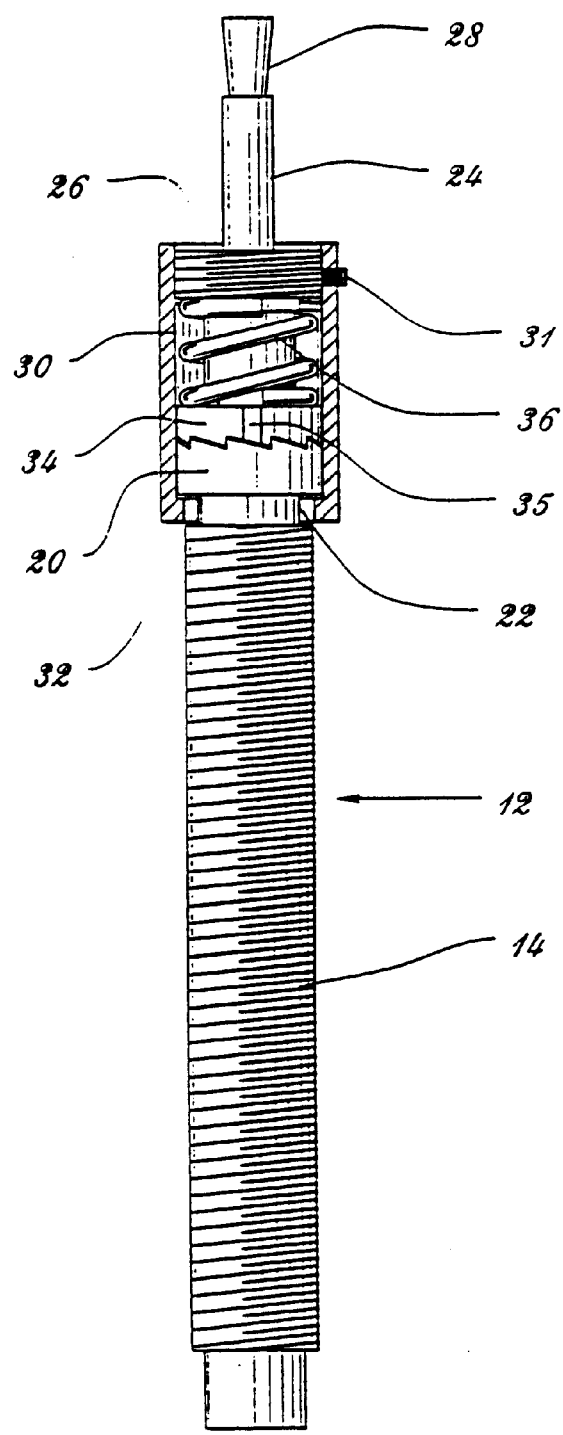
FIG. 6 is an exploded elevation and a partially longitudinal section of one of the fixation pins in accordance with the invention.
Figure 6:
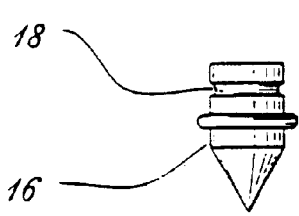
Figure 7:
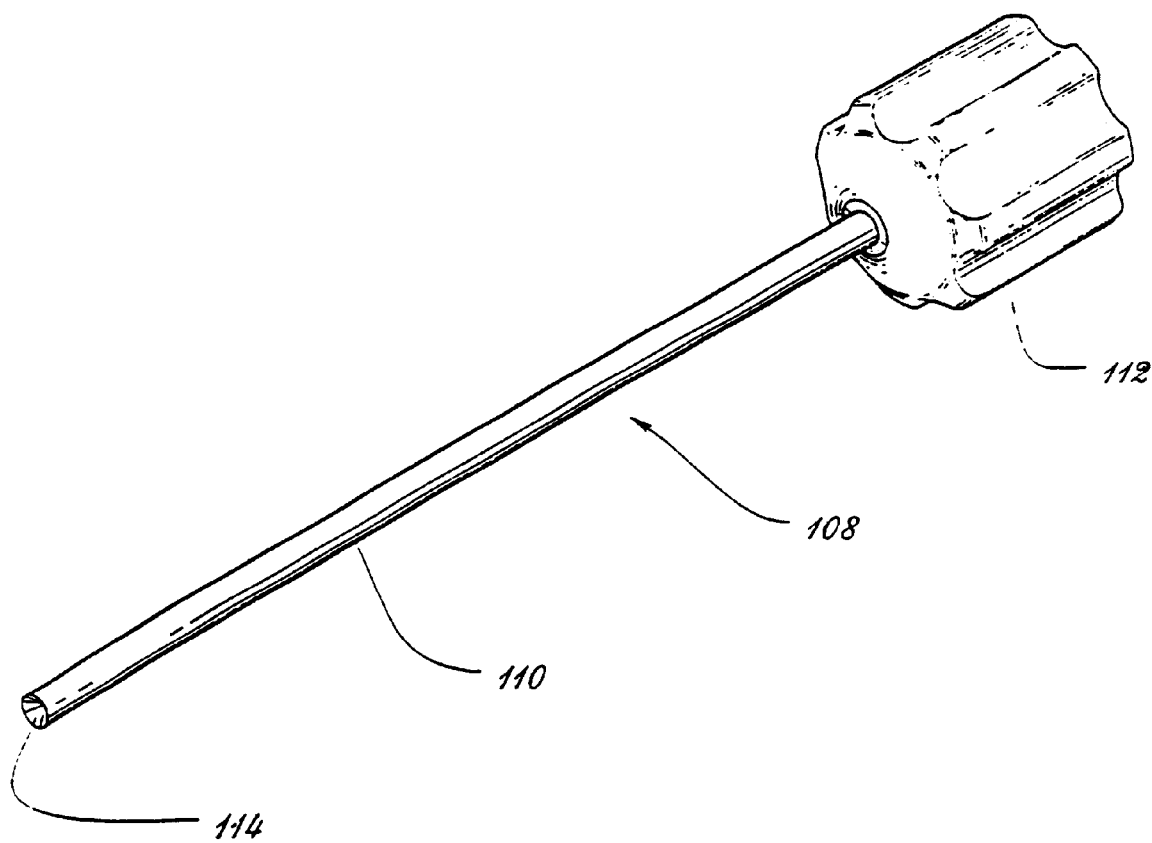
FIG. 7 is a perspective view of the scalp punch in accordance with the invention.

Referring to FIG. 6, each fixation pin 12 comprises an externally threaded cylindrical body 14 which can be screwed in any through bore 10; a pointed tip 16, with an O-ring (not shown) in a groove 18 thereof, is tight fitted within the distal end of hollow body 14; a ratchet toothed annulus 20 is formed at the proximal end of body 14 and defines a groove 22 under annulus 20. The distal end of a guide shaft 24, coaxial with body 14, is freely inserted into and guided by a cavity at the center of ratchet tooth annulus 20. Guide shaft 24 has an intermediate enlarged portion 26 which is externally threaded and is terminated at its proximal end by an hexagonal nut 28 for insertion into the chuck of a power drill.

A knurled, sleeve-like knob 30 is internally threaded and can be adjustably screwed on the intermediate enlarged portion 26 of guide shaft 24; a set screw 31 serves to fix the knob 30 in adjusted position on enlarged portion 26. The distal end of the sleeve-like operating knob 30 forms a shoulder 32 rotatably engaging grove 22 of body 14. A floating ratchet toothed carrying ring 34 and a compression coil spring 36 surround the guide shaft 24. Spring 36 is located intermediate floating ratchet ring 34 and enlarged portion 26. The teeth of floating ring 34 are biased by spring 36 into engagement with the ratchet teeth of annulus 20. The floating ring 34 has a keyway 35 for receiving a locking screw (not shown) carried by the knob 30 for preventing rotation of floating ring 34 but not its axial movement relative to knob 30. Knob 30 is screwed on enlarged portion 26 to an adjusted relative axial position and then locked by set screw 31; this determines the maximum pressure to be exerted by the fixation pin on the patient's skull.

The body 14 of the fixation pin 12 is screwed by knob within the through bore 10 of the headclamp 2 until the desired pressure is obtained at which time the teeth of the floating ratchet ring 34 start to slip on the teeth of the ratchet teeth annulus 20. Therefore, the pre-determined maximum pressure to be exerted by the fixation pin on the patient's skull is not exceeded.

Instead of manually rotating knob 30, the pin body 14 can be screwed within the headclamp through bore 10 by means or a power drill, the chuck of which engages the hexagonal nut 28 of guide shaft 24.

Referring to FIG. 1, an articulated arm 38 is selectively secured into any one of the through bores 10 of headframe 2; this articulated arm comprises a base joint 40, a locking pin 42, a first arm section 44, an intermediate joint 46, a second arm section 48 with an outer joint 50, and a third arm section (not shown) extending from the outer joint 50. Each joint 40, 46, 50 can be clamped in adjusted position by means of a clamping knob 52. Each arm section can be rotated about three axes at their respective joints.

Base joint 40 has a threaded nipple to be screwed into anyone of the through bores 10 and locked in position by the locking ring 42 which is screwed on the nipple.

The distal or third arm section consists of a externally threaded rod for screwing a double chuck 54 thereover.

This double chuck 54 consists of a body 56 with a body extension 58 having an internally threaded bore 60 for receiving the third arm section. Body 56 has opposite base faces 62 and two cylindrical cavities 64 disposed side by side; each cavity has a step 66 defining an opening 68 at one of base faces 62. A cover plate 70 is secured to the opposite base face by means of screws 72; cover plate 70 has two openings 74 disposed side by side in respective register with the two cylindrical cavities 64. Openings 68 and 74 have the same diameter which is smaller than the diameter of cavities 64. Each cylindrical cavity 64 receives with a sliding fit a ball collet 76 which has a diametral through bore 78 which is internally threaded. The ball collet 76 can freely rotate within the cylindrical cavity 64 but cannot be axially displaced therein because it abuts the step 66 and the inside face of the cover plate 70.

An externally threaded sleeve 80 is screwed within the through bore 78 of each ball collet 76. Sleeve 80 has an externally threaded, longitudinally slit, free end portion 82. A ball collet locking screw 84 is screwed within one of the side faces of the body 76, opposite each ball collet 76 to releasably lock the ball collet in adjusted rotated position. Locking screw 84 has a double arm head 86 for applying sufficient torque.

A locking nut 88 is threaded with an interference fit in the longitudinally slit, free end portion 82 to clamp in axially adjusted position any cylindrical surgical instrument slidably fitted within the sleeve 80.

Figure 2:
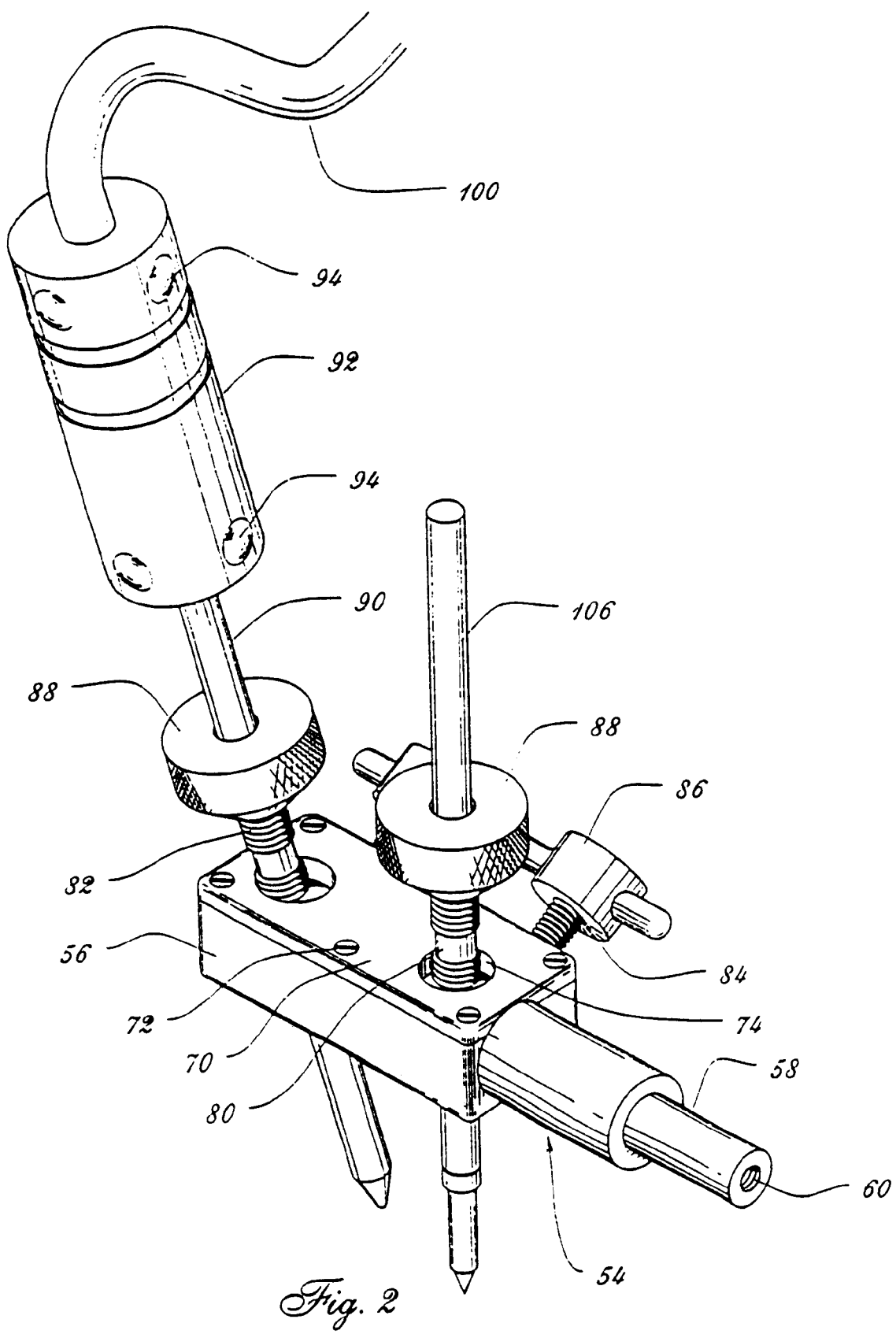
FIG. 2 is a perspective view of the double chuck at the distal end of the articulated arm and into which a computer probe and a stabilizing pin are secured.

For instance, a cylindrical computer probe 90 shown in FIG. 2, is axially inserted within the sleeve 80 of one of the two chucks, and locked in the desired orientation by screwing locking screw 84 to clamp the ball collet 76 in body 56; then computer probe 90 is axially positioned within the sleeved 80 and once the desired axial position is obtained, locking nut 88 is screwed to cause inward gripping of the free end portion 82 on the probe 90.

This probe 90 is a computer guided probe. It has an enlarged outer handle 92 provided with several Light Emitting Diodes LED 94 powered by a cable 100 connected to a computer 102 with a screen and keyboard. At least two cameras 104, which are spacedly located in the operating room, photograph LED's 94 and feed data to computer 102 which can constantly determine and display the spatial position of the probe in the operating room.

Computer 102 was previously loaded with 3-D image data taken from patient's head scanning, for instance by magnetic resonance imaging and has co-registration software so that the probe may be actually positioned at the exact site and along a specific trajectory of the lesion or structure within the patient's brain. Such a system is already known.

Another known type of such computer guided system is also manufactured and sold by Brain Lab U.S.A. Inc. of 3210 Hanson Way, Palo Alto, Calif., U.S.A. In this system, reflector marker spheres are mounted on the probe handle instead of LED's 94 and the cameras capture the reflected images of said marker spheres and the images are converted to spatial positions of the probe which are displayed on the computer screen. Naturally, additional such markers can be adhered to the head at selected positions to coregister the probe with the virtual head on the computer screen.

In addition and subsequently to probe 90, a number of instruments can be serially inserted through sleeves 80 of the double chuck 54. Such instruments include a stabilizing pin 106, a scalp punch 108, a twisted drill 116 and a ruler guide 128, and brain cannula.

Pin 106 includes a cylindrical body with a pointed tip to engage the scalp of the patient's head.

Scalp punch 108 consists of a rod 110 sized to slidably sit within chuck sleeve 80 and is provided with an enlarged head 112 at its distal end and with a central recess 114 at its proximal said recess defining an annular cutting edge. The scalp punch is used as follows: It is guided in a sleeve 80 of the double shuck 54 and held by the latter in the desired spatial position and orientation and rotated to cut out a scalp button.

Figure 8:
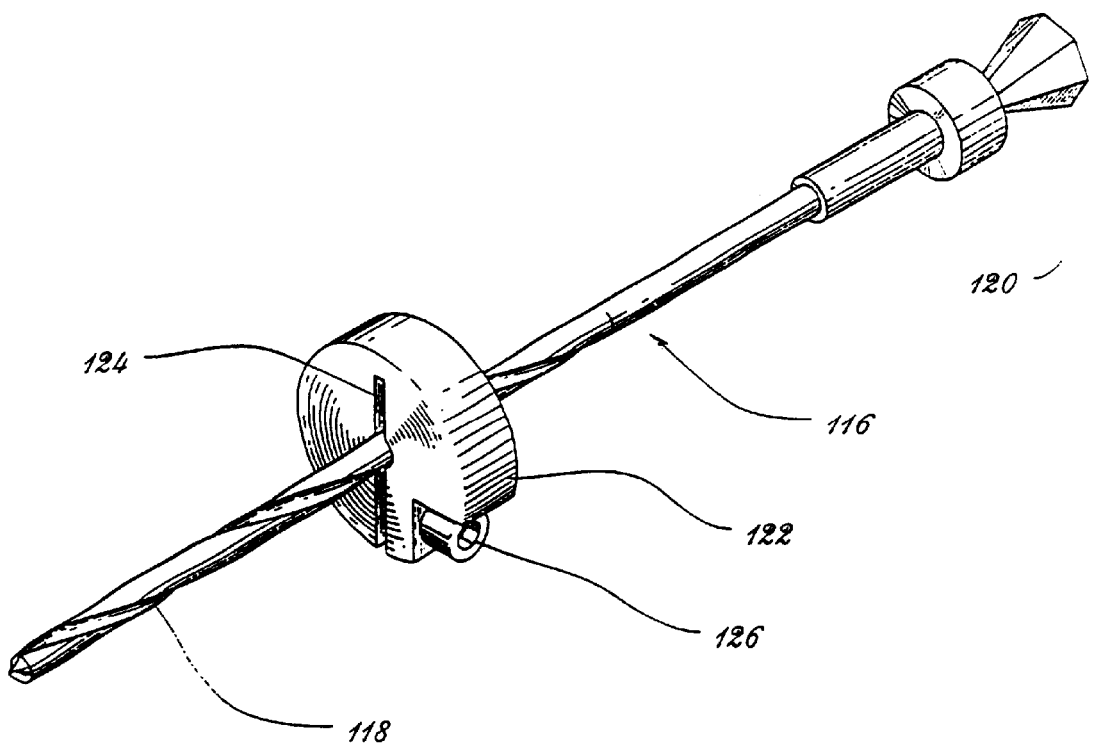
FIG. 8 is a perspective view of the twisted drill with its stopper in accordance with the invention.
Figure 9:
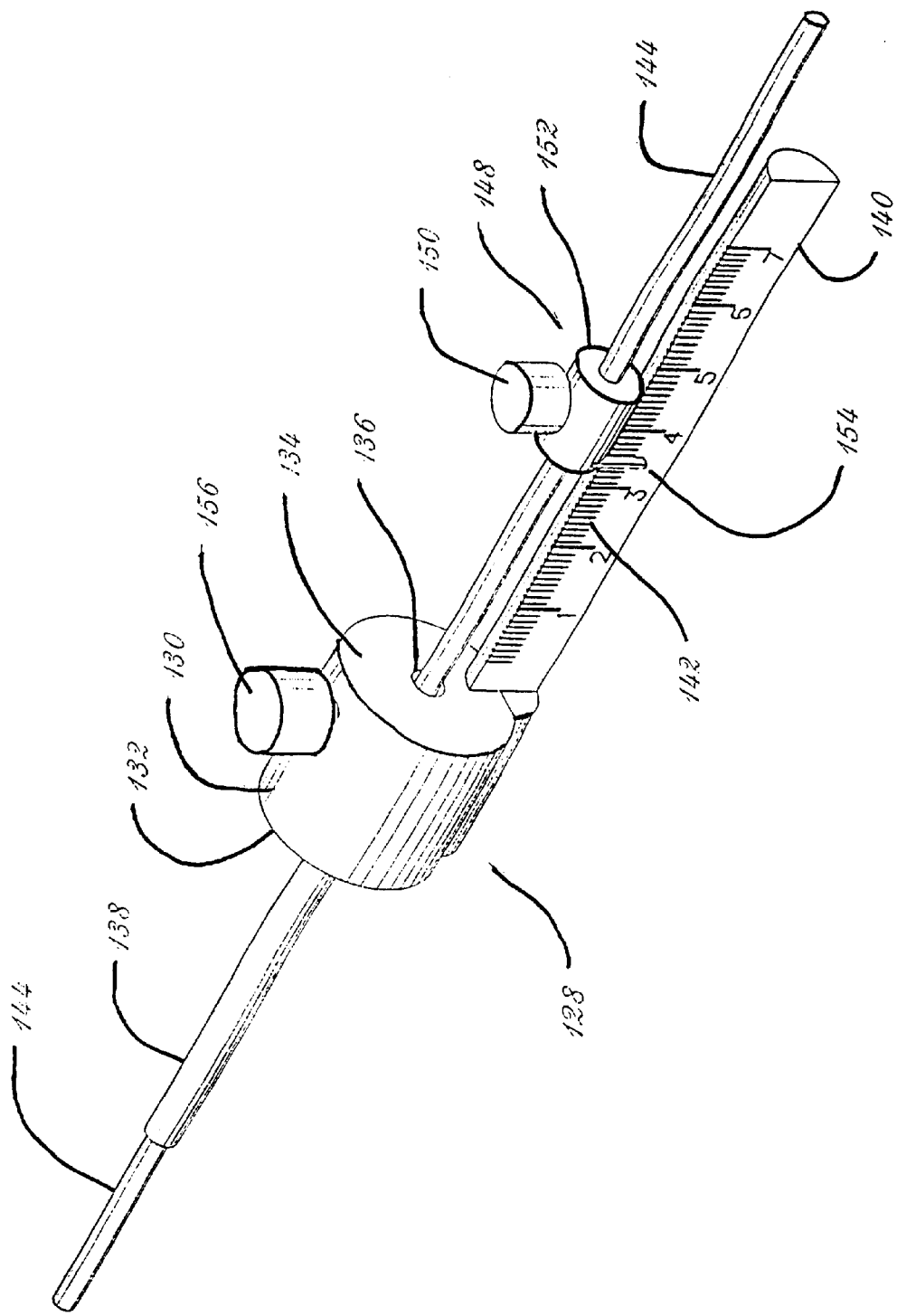
FIG. 9 is a perspective view of the ruler guide in accordance with the invention.

Twisted drill 16 (see FIG. 8) can also be guided through sleeve 80: this twisted drill includes a cylindrical body 118 sized to slidably fit sleeve 80 and provided at its distal end with a rotatable chuck engaging head 120 which inwardly tapers towards body 118. This tapered head 120 allows a slight misalignment of a hand held power tool relative to the chuck axis between the rotatable chuck of a hand held power tool used to rotate drill 116 so that drill 116 may be positively guided by the sleeve 80 without producing excessive torsional forces on the chuck 54; an out of round drill hole in the patient's skull is thus avoided. A stop collar 122 limits the depth of penetration of the drill bit 116 into the skull table or dura; stop collar 122 has a radial slit 124 and a screw 126 is threaded accross slit 124 to clamp the collar in adjusted position on the twisted drill.

The ruler guide 128 includes a cylindrical body 130 having an inner end face 132 and an outer face 134 which are parallel to each other and normal to the body axis. A through bore 136 extends axially of body 130 and a guide tube 138 is secured to body 130, protrudes from the inner end face 132, is coaxial with through bore 136 and is in communication therewith. A ruler strip or bar 140, for instance of semi-cylindrical cross-section for rigidity, is secured to body 130 and extends from the outer face 134 thereof, it had a graduation 142 expressed in millimeters and increasing from 0 to 7 cm in a direction away from body 130. The reading edge of the ruler bar 140 is adjacent and parallel to the axis of the through bore 136. A canula 144 is inserted with a sliding fit within through bore 136 and guide tube 138. This cannula is open at both ends and is fitted with a position indicator 148 which is fixed on the canula 144 in adjusted position by a set screw 150. Position indicator includes a body 152 having an indicator finger 154 overlying graduation 142.

Another set screw 156 is screwed within the body 130 to lock the canula 144 in longitudinally adjusted position within the body. Guide tube 138 is sized to slidably fit the sleeves 80 of the double chuck 54.

Referring to FIG. 1, it is seen that semi-circular headclamp 2 is firmly secured to the patient's head, by means of at least three fixation pins 12 with two pins facing each other and radially inwardly directed from the headclamp. This headclamp is outwardly spaced from head H, and therefore practically the entire head surface is accessible even underneath the headclamp. Articulated arm 38 and double chuck 54 form an assembly which occupies a minimum of space and therefore constitutes a minimum obstruction for the surgeon's work.

Moreover, two or three assemblies of an articulated arm 38 and double chuck 54 may be positioned on the frame at the through bores 10 which are still available and not occupied by the fixation pins 12. Therefore, several sites (for instance bilaterally on the patient's head or in his brain may be reached during the same stereotactic procedure.

The clamping knobs 52 of articulated arm 38 can be easily manipulated by one hand to firmly position the double chuck 54 in the required position spaced from the applicant's skull. The three joint system of the articulated arm 38 allows an exceptional range of free movement. A specially designed wrench is used to further tighten the joints 38 once the optimal trajectory has been correlated between the computer and the articulated arm.

Each chuck of double chuck 54 can be locked securely by ball collet locking screw 84 for orientation of the inserted instrument and then the instrument can be clamped in adjusted longitudinal position by the instrument locking screw 88 which is independent of the first locking screw 84.

Since instrument locking screw 88 protrudes from the end of sleeve 80, it can also be used in conjunction with stop collar 122 on the drill 116 as a fine adjustment of the drill skull penetration to avoid accidental plunging through the dura. Usually, the outside chuck is used for receiving the viewing probe 90 to select the best trajectory, to maintain the proper angulation and to insert a cannula or an electrode on target, such as cannula 144 of the ruler device 128.

The inside chuck normally serves to receive stabilizing pin 106 which is applied to the skull and provides a necessary support for safe skull penetration with drill 116. This sharp pin 106 also helps to maintain the double chuck 54 in the precise desired spatial position while using the outside chuck to hold the ruler guide 128 in the proper orientation and spatial position.

Placement of depth electrodes using the apparatus of the present invention is now described to detect the presence of a suspected but unconfirmed epileptic focus and to study the early spread of an epileptic seizure.

Target selection (based o MRI imaging) can be done the day prior to surgery or while the patient is being put asleep and prepared for surgery. Using the computer software, a series of dots and tags are placed over the structures to be reached using an identification code such as RA for right, etc. For selection of a deep target such as amygdala, and two dimensional software program reconstruction displays are used. For the surface cortical (epidural) target, the 3D reconstruction is used because it shows the gyral and suical anatomy with a greater degree of precision.

Use of the articulated arm enables the proper selection of the trajectory to the target, using the software trajectory mode. The computer guided probe 90 is manipulated until the trajectory tract reaches the distal target through an avascular channel. If significant blood vessels are encountered, the angle is changed by manipulating the ball collet 76. The probe is then immobilized in place by tightening the joints of the articulated arm with a small wrench. Further stabilization is accomplished by inserting the sharp stabilizing pin 106 against the skull as shown.

A scalp button of about three millimeter diameter is removed using the scalp punch 108 inserted into the sleeve 80 of the inner chuck as a guide.

With the computer software in the trajectory mode, it is possible to precisely assess the bone thickness at the site of trephination. The drill 116 is used to perforate the bone, its stopper 122 preventing it from accidentally overshooting and perforating the dura while allowing complete perforation of the inner table. Good control of the drill bit is obtained by the use of a low revolution battery powered commercial drill. A hollow anchoring bone peg is then inserted into the hole, the narrow end of the peg is gently hammered into position in the drill hole until its shoulder is against the skull. If the peg alignment is not perfectly in line with the electrode path, it is corrected at this point.

The purpose of the bone peg is two fold; first, the outer end of the peg becomes the reference point to measure the length of insertion, that is the distance between the peg point and the distal target point. The second crucial role of the peg is to completely immobilize the recording electrode.

Dural coagulation is performed through the bone peg. The dura is perforated with a sharp coagulating electrode, insulated except for its tip. This electrode is manipulated inside a shaft which fits the chuck. When the characteristic resistance of the dura is encountered, a low current is passed while gentle pressure is maintained over a 3–4 millimeter distance. When the typical dural yielding is felt, the electrode is withdrawn. The distance between the outer ring of the skull peg and the final target site is then calculated with the software by recording with the computer controlled probe 90, both the position of the outer extent of the peg and the pre-selected target.

The ruler guide 128 is then inserted into the chuck and the brain cannula 144 is inserted until its tip touches the outer extent of the skull peg. The distance between the latter point and the target point is then measured along the canula and marked by the indicating stopper 148 fixed to the cannula.

The brain cannula 144 is then gently pushed through the dural opening until the target is reached. The stylet of the brain canula is then replaced by the recording electrode, the distal end of which is immobilized on target with an alligator clamp. This clamp is mounted on a rod which is inserted in the inner chuck in place of the sharp pin 106 which has by then terminated its role of stabilization. The inner chuck can be made parallel with the outer chuck at this point, to keep the distance uniform between the alligator clamp and the recording electrode.

After withdrawing the canula and leaving in the recording electrode on target, final immobilization of the electrode is accomplished by inserting an acrylic mixture in the distal extent of the bone peg and around the electrode. The electrode is free from the insertion system, it is then identified with a tag, for instance RA for right amygdala, fixed to its extremity.

Several electrodes can be inserted in this manner (bilaterally simultaneously) and they are connected in a bundle and eventually brought outside the head dressing.

We claim:

1. A chuck for neurosurgical stereotactic procedures comprising a body, a body extension to firmly secure said body to the distal end of an articulated arm, the body having a quadrangular cross-section with opposite base faces and two opposite side faces, a cylindrical body cavity having a first, circular, cavity opening at one of said two base faces, a cover plate removably covering the other one of said two base faces and having a second, circular, cavity opening in register with said first cavity opening, said first and second, circular, cavity openings having a smaller diameter than the diameter of said cylindrical body cavity, a ball member having a diametral through bore, located in said body cavity with a sliding fit and free to rotate about its center, a ball tightening member carried by said body, and protruding from one of said side faces to clamp said ball member in a selected oriented position of its through bore, a sleeve extending within said through bore and firmly secured to said ball member, said sleeve having an externally threaded, longitudinally slit, free end portion protruding from said body through at least one of said cavity openings and a locking nut surrounding and threaded on said free end portion and having an interfering fit with said slit free end portion to clamp in a selected longitudinal position, a surgical instrument of a cross-sectional size and shape to have a sliding fit with the inside of said sleeve, whereby the precise orientation and the longitudinal position of said instrument relative to said body can be successively and independently effected by respectively actuating said ball tightening member and said locking nut.

2. A chuck as defined in claim 1 wherein said locking nut protrudes from said free end portion of said sleeve.

3. A double chuck, wherein there are two chucks as defined in claim 2, disposed side by side, within said body.

4. A double chuck, wherein there are two chucks as defined in claim 1, disposed side by side, within said body.

5. A chuck as in claim 1, further including a twisted drill for fitting the rotatable chuck of a hand held power drilling tool, said drill comprising a helically fluted cylindrical body with a rotatable head, said head engageable by said rotatable chuck, said cylindrical body adapted to slidably fit within a guiding sleeve, said head inwardly tapered toward said cylindrical body and defining a distal free edge which is solely gripped by said rotatable chuck so that said body become inclined relative to the rotating axis of said rotatable chuck.

6. A twisted drill bit as defined in claim 5, wherein said head has a polygonal cross-section.

7. A twisted drill bit as defined in claim 5, further including a stop collar surrounding and slidable on said body, and a manually actuated releasable clamping device carried by said collar and releasably clamping said collar in a longitudinally adjusted position on said body.

8. A ruler for use during frameless stereotactic procedures comprising a body having first and second parallel end faces and a through bore normal to said end faces, a tubing fixed to said body and protruding from said first end face in a first direction, said tubing coaxial with and communicating with said through bore, a graduated ruler strip secured to said body and protruding from said second end face in a second direction opposite to said first direction, said strip having an edge parallel with and close to the axis of said through bore, said ruler calibrated to indicate the distance from said second end face of a selected point on a surgical instrument inserted within said through bore and within said tubing; said ruler for calculating the depth of penetration of a brain cannula to a predetermined distal target referenced to an entrance point on the skull.

9. A device for stabilizing one end of an articulated arm relative to a patient during an operative procedure, the other end of said articulated arm is adapted for attachment to a clamp, the device comprising:
- a body member adapted to be secured at the free end of the articulated arm, the body member having a pair of chucks, one of which is capable of releasably guiding a surgical instrument, the other of which is capable of releasably securing a stabilizing member against the patient, to thereby stabilize the free end of the articulated arm during the operative procedure.

10. The device according to claim 9 for use in a stereotactic apparatus further comprising a support for holding the patient, said articulated arm adapted to be secured relative to the support.

11. The device according to claim 10, wherein said articulated arm further includes a plurality of securable joints.

12. The device according to claim 10, wherein said stereotactic apparatus is frameless.

13. The device according to claim 9, wherein securing of said stabilizing member substantially maintains said body member in a selected spatial relationship with respect to said patient.

14. The device according to claim 9 further comprising a first locking mechanism and a second locking mechanism connected to at least one of said pair of chucks, said first locking mechanism to releasably lock the chuck in a selected orientation and said second locking mechanism to releasably lock the corresponding instrument or stabilizing member contained in said chuck in a selected axial position.

15. The device according to claim 14, wherein said first locking mechanism and said second locking mechanism at actuated independently of each other.

16. A method for stabilizing one end of an articulated arm relative to a patient during an operative procedure, the other end of said articulated arm is adapted for attachment to a clamp, said method comprising the steps of:
- a) securing a stabilizing device to the free end of the articulated arm, the stabilizing device having a pair of chucks;
- b) securing a stabilizing member to one of said pair of chucks for holding one end of said member against the patient; and
- c) using the other of the chucks for guiding a surgical instrument during the operative procedure, wherein the free end of the articulated arm is stabilized during the operative procedure.

17. The method according to claim 16, wherein the step of securing said stabilizing member to one of said pair of chucks substantially maintains said pair of chucks in a selected spatial relationship with respect to said patient.

18. The method according to claim 16 further comprising the step of locking the surgical instrument in said other of said chucks in a selected orientation and a selected axial position.

19. The method according to claim 18, wherein the locking of said surgical instrument in said selected orientation and said selected axial position are actuated independently of each other.

20. The method according to claim 18, further comprising a step of moving the stabilizing device and the patient in substantial unison for maintaining a selected spatial relationship between said patient and said stabilizing device.

21. The method according to claim 16, further comprising a step of moving the stabilizing device and the patient in substantial unison for maintaining a selected spatial relationship between said patient and said stabilizing device.

* * * * *